United States Patent [19]
Katritzky et al.

[11] Patent Number: 5,770,775
[45] Date of Patent: Jun. 23, 1998

[54] METHOD FOR PREPARING 3,3-DIMETHYLBUTYRALDEHYDE

[75] Inventors: Alan R. Katritzky, Gainesville, Fla.; Indra Prakash, Hoffman Estates, Ill.

[73] Assignee: The NutraSweet Company, Deerfield, Ill.

[21] Appl. No.: 796,443

[22] Filed: Feb. 10, 1997

[51] Int. Cl.$^6$ ................................................ C07C 45/51
[52] U.S. Cl. ........................ 568/450; 568/427; 426/548
[58] Field of Search .............................. 568/450

[56] References Cited

U.S. PATENT DOCUMENTS

| | | | |
|---|---|---|---|
| 5,480,668 | 1/1996 | Nofre et al. | 426/548 |
| 5,510,508 | 4/1996 | Claude et al. | 560/41 |

OTHER PUBLICATIONS

Yanagisawa et al; J.Chem.Soc., Chem.Commun., pp. 2103–2104, 1994.

Mischitz et al; Tetrahedron Asymmetry, #6, pp. 1261–1272, 1995.

Kryukov et al; Neftekhimiya et al; 19(5), pp. 762–766, 1979.

Smith, J.G., Synthesis, 629 (1984).

Sudha, R. et al., J. Org. Chem. 61, 1877 (1996).

Yanagisawa, A. et al., J. Chem. Soc. Chem. Commun. 2103 (1994).

*Primary Examiner*—Gary Geist
*Assistant Examiner*—S. Padmanabhan
*Attorney, Agent, or Firm*—Fitzpatrick, Cella, Harper & Scinto

[57] ABSTRACT

A method is disclosed for preparing 3,3-dimethylbutyraldehyde by isomerization of 3,3-dimethylepoxybutane with a basic lithium salt which in turn may be prepared by oxidation of dimethylbutane. The method provides an economical means of preparing 3,3-dimethylbutyraldehyde.

2 Claims, No Drawings

METHOD FOR PREPARING 3,3-DIMETHYLBUTYRALDEHYDE

BACKGROUND OF THE INVENTION

1. Field of the Invention

This invention relates to a method for preparing 3,3-dimethylbutyraldehyde in a highly economical manner by regioselective isomerization of an epoxide in the presence of a basic lithium salt.

2. Related Background Art

Rearrangement of epoxides to carbonyl compounds has long been known. See, e.g., Smith, J. G. Synthesis, 629 (1984). For example, epoxides have been converted to aldehydes in a regiospecific manner through the use of lithium perchlorate in diethyl ether (LPDE). Sudha, R., et al. J. Org. Chem. 61, 1877 (1996). However, this reference discloses that acyclic terminal olefin epoxides, such as 1,2-epoxyhexane did not reacts in the LPDE medium.

Yasue, K. et al., J. Chem, Soc. Chem. Commun. 2103 (1994) discloses the reaction of various 1,2-epoxyalkanes with lithium 2,2,6,6-tetramethylpiperidine to produce the corresponding aldehydes. However, there is no guidance provided as to the reactivity of 1,2-epoxylalkanes, such as 3,3-dimethyl-1,2-epoxybutane, that are sterically hindered at the carbon alpha to the epoxide ring.

3,3-Dimethylbutyraldehyde is an intermediate that is useful is the preparation of the sweetener N-[N-(3,3-dimethylbutyl)-L-α-aspartyl]-L-phenylalanine disclosed in U.S. Pat. No. 5,480,668 and U.S. Pat. No. 5,510,508. Accordingly, a method for preparing that intermediate which is both economical and specific is highly desired.

SUMMARY OF THE INVENTION

This invention relates to a method for preparing 3,3-dimethylbutyraldehyde comprising the step of isomerizing 3,3-dimethyl-1,2-epoxybutane in the presence of a basic lithium salt. A preferred basic lithium salt is lithium 2,2,6,6-tetramethylpiperidine (LiTMP). The invention also relates to the above-described method further comprising the step of oxidizing dimethylbutene to form 3,3-dimethyl-1,2-epoxybutane prior to the step of isomerization.

The method of this invention allows for the preparation of 3,3-dimethylbutyraldehyde in a reproducible and highly economical manner so that use of the aldehyde in the preparation of a sweetener derived from aspartame is commercially practicable.

DETAILED DESCRIPTION OF THE INVENTION

The method of the invention provides a means for the regiospecific isomerization of 3,3-dimethyl-1,2-epoxybutane to form 3,3-dimethylbutyraldehyde through the use of a basic lithium salt.

The lithium salts, include, for example, lithium trimethylpiperidine (LiTMP), lithium bromide/alumina, lithium perchlorate, lithium diisopropylamine and the like. Lithium trimethylpiperidine is most preferred.

The preparation of 3,3-dimethylbutyraldehyde in accordance with one embodiment of the invention comprises mixing 3,3-dimethyl-1,2-epoxybutane with a basic lithium salt for a period of time and at a sufficient pressure and temperature to form 3,3-dimethylbutyraldehyde. Generally, the temperature of the reaction is held between about 0° C. to about 20° C. and the reaction pressure can be atmospheric. However, any reaction temperature and pressure may be employed that results in the production of 3,3-dimethylbutyraldehyde. The reaction time is typically between about 2 and about 24 hours.

In a preferred embodiment of this invention, the method includes the step of preparing 3,3-dimethyl-1,2-epoxybutane by oxidation of dimethylbutene prior to the step of isomerization. An example of this two step synthesis is illustrated below.

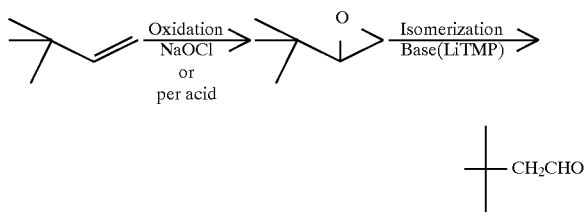

The step of oxidation is typically accomplished by epoxidation of dimethylbutene with an oxidizing agent, See e.g., Mischitz, M., et al., Tetrahedron: Asymmetry 6, 1261–1272 (1995). Preferred oxidizing agents include NaOCl/catalysts (such exemplary catalysts include Mn-salen or Mn-porphyrins), hydrogen peroxide/catalysts (such exemplary catalysts include tungsten, rhenium or vanadium), and peracids. Exemplary peracids include without limitation perbenzoic acid, metachloroperbenzoic acid, monoperoxyphthalic acid, trifluoroperacetic acid, magnesium monoperoxyphthalate, peracetic acid. Other oxidizing reagents include peroxides such as, for example, hydrogen peroxide, t-butylhydroperoxide and dibenzoylperoxide.

Generally, the oxidizing agent is present in an amount between about 100 to about 105 percent by molar weight of the dimethylbutene. However, any amount of oxidizing agent may be employed that results in the oxidation of a substantial amount of dimethylbutene. Typically, the step of oxidation is conducted at a temperature of between about −5° C. to about 0° C. and at atmospheric pressure with a reaction time of about 24 hours, although other reaction temperatures and pressures may be used as will be readily apparent to those skilled in the art.

The Examples which follow are intended as an illustration of certain preferred embodiments of the invention, and no limitation of the invention is implied.

EXAMPLE 1

Preparation of 3,3-Dimethyl-1,2-epoxybutane

To a stirred solution of 3-chlorobenzoic acid (30.2g; 87.58 mmol) in methylene chloride (230 mls) was added 3,3-dimethyl-l-butene (7.5g; 84.6 mmol). The solution was maintained at about 0° C. for 24 hours with stirring. The 3-chlorobenzoic acid by product was separated from the methylene chloride solution by shaking with an excess of 10 per cent sodium hydroxide solution. The residual alkali was removed by washing with water and then the methylene chloride solution was dried over anhydrous magnesium sulfate and filtered. The filtrate was distilled with a fractionating column and after the methylene chloride was removed, the 3,3-dimethyl-1,2-epoxybutane distilled over at 94°–96° C./760 mmHg as a colorless liquid. The yield was approximately 4.5 grams (53%).

EXAMPLE 2

Preparation of Dinitrophenylhydrazine Adduct of 3,3-Dimethylbutyraldehyde

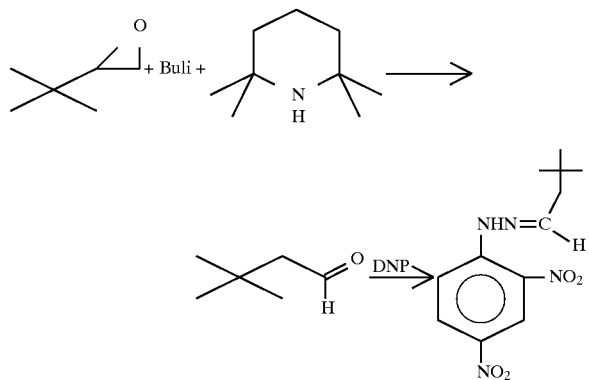

To a solution of 2,2,6,6-tetramethylpiperidine (4.06g; 28.75 mmol) in tetrahydrofuran (57.5 mL) was added dropwise a solution of n-butyllithium in cyclohexane (2M, 14.38 mL; 28.75 mmol) at 0° C. under an argon atmosphere. After being stirred for about 30 minutes, a solution of 3,3-dimethyl-1,2-epoxybutane (1.466 g; 11.5 mmol) in tetrahydrofuran (11.5 mL) was added at 20° C. and the reaction mixture was stirred at this temperature for another 15 hours. The reaction mixture was treated with a saturated aqueous ammonium chloride solution under nitrogen at 20° C. and extracted with diethyl ether. The diethyl ether layer was dried over anhydrous magnesium sulfate and filtered.

In a separate flask, 2,4-dinitrophenylhydrazine (DNP, 4.9 g) was suspended in methanol (98 mL) and concentrated sulfuric acid (7.8 mL) was added cautiously. The solution was filtered off and added to the above diethyl ether solution. The mixture was concentrated to 60 mL by removing the solvent under reduced pressure and then water was added to it. The organic layer was separated, and the aqueous layer was extracted with diethyl ether (2×40 ml). The combined organic layer was dried over anhydrous magnesium sulfate, then filtered and the filtrate concentrated to dryness. The crude compound was purified by column chromatography on silica gel using chloroform/hexane (4:1) as an eluent to give 1.9 g (60%) of orange solid.

MP 149°–151° C.; $^1$H NMR (CDCl$_3$) δ(TMS) 1.04 (s 9H, t-Bu), 2.31(d, 2H, CH$_2$), 7.62 (t, 1H, CH), 7.93 (d, 1H, ArH), 8.27 (dd, 1H, ArH), 9.10 (s, 1H, ArH), 11.06 (s, 1H, NH). Anal. Calcd for C$_{12}$H$_{16}$N$_4$O$_4$: C, 51.42; H, 5.75; N, 19.99. Found: C, 51.32; H, 5.71; N, 19.89.

Other variations and modifications of this invention will be obvious to those skilled in this art. This invention is not to be limited except as set forth in the following claims.

What is claimed is:

1. A method for preparing 3,3-dimethylbutyraldehyde comprising the step of isomerizing 3,3-dimethyl-1,2-epoxybutane in the presence of a basic lithium salt to form said 3,3-dimethylbutyraldehyde.

2. A method according to claim 1, wherein said basic lithium salt is lithium trimethylpiperidine.

* * * * *

UNITED STATES PATENT AND TRADEMARK OFFICE
CERTIFICATE OF CORRECTION

PATENT NO.   : 5,770,775
DATED        : June 23, 1998
INVENTOR(S)  : ALAN R. KATRITZKY ET AL.

It is certified that error appears in the above-identified patent and that said Letters Patent is hereby corrected as shown below:

TITLE PAGE

Item: [56] "et al; J. Chem. Soc.," should read
    --et al., J. Chem. Soc.,--;

COLUMN 1

Line 19, "reacts" should read --react--;

COLUMN 2

Line 22, "agent," should read --agent.--;
    Line 58, "by product" should read --by-product--.

Signed and Sealed this

Thirteenth Day of July, 1999

Attest:

Attesting Officer

Q. TODD DICKINSON

Acting Commissioner of Patents and Trademarks